US008114607B2

(12) United States Patent
Yokoyama

(10) Patent No.: US 8,114,607 B2
(45) Date of Patent: Feb. 14, 2012

(54) TYPE IV COLLAGEN-LIKE IMMUNOREACTIVE PEPTIDE

(76) Inventor: Tsukao Yokoyama, Tokyo (JP)

( * ) Notice: Subject to any disclaimer, the term of this patent is extended or adjusted under 35 U.S.C. 154(b) by 147 days.

(21) Appl. No.: 12/304,140

(22) PCT Filed: Jun. 12, 2007

(86) PCT No.: PCT/JP2007/061779
§ 371 (c)(1),
(2), (4) Date: Feb. 9, 2009

(87) PCT Pub. No.: WO2007/145192
PCT Pub. Date: Dec. 21, 2007

(65) Prior Publication Data
US 2009/0186044 A1    Jul. 23, 2009

(30) Foreign Application Priority Data

Jun. 12, 2006 (JP) .................................. 2006-187186
May 24, 2007 (JP) ................................ 2007-137856

(51) Int. Cl.
*A61K 38/04* (2006.01)
*G01N 33/53* (2006.01)
(52) U.S. Cl. ........................ 435/7.1; 530/328; 530/326
(58) Field of Classification Search .................... None
See application file for complete search history.

(56) References Cited

U.S. PATENT DOCUMENTS 5,741,652 A    4/1998  Shibuya et al.
7,122,517 B2 * 10/2006  Hudson et al. ................ 514/13.3

FOREIGN PATENT DOCUMENTS

| EP | 1 712 564 A1 | 10/2006 |
| JP | 08-100000 A | 4/1996 |
| JP | 2000-214163 A | 8/2000 |
| JP | 2002-173446 A | 6/2002 |
| JP | 2002-302457 A | 10/2002 |
| WO | 2005/082940 A1 | 9/2005 |

OTHER PUBLICATIONS

Sugihara et al. Experimental anti-GBM glomerulonephritis induced in rats by immunization with synthetic peptides based on six alpha chains of human type IV collagen. Journal of Pathology, vol. 178: 352-358 (1996).*
Zhou et al. Structure of the human type IV collagen COL4A5 gene. J Biol Chem. Mar. 4, 1994;269(9):6608-14.*
Kuroda et al. Expression of type IV collagen in the developing human kidney. Pediatr Nephrol 12:554-558, 1998.*
Colman PM. Effects of amino acid sequence changes on antibody-antigen interactions. Res Immunol. 145(1):33-36, 1994.*
Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.*
Lederman S, et al. A single amino acid substitution in a common African allele of the CD4 molecule ablates binding of the monoclonal antibody, OKT4. Mol Immunol. 28(11):1171-81, 1991.*
Li CH, Yamashiro D, Tseng LF, Chang WC, Ferrara P. beta-Endorphin omission analogs: dissociation of immunoreactivity from other biological activities. Proc Natl Acad Sci U S A. 77(6):3211-3214, 1980.*
M.A. Haralson et al., "Extracellular Matrix IRL Press/Oxford University Press Oxford New York", Dec. 1995, (extract plus p. 102).
"Jin to Toseki (Kidney and Dialysis) Jul. 2005, vol. 59, No. 1, Tokyo Igakusha" (extract plus pp. 8 & 160).
B. Hudson et al., "Type IV Collagen: Structure, Gene Organization, and Role in Human Diseases", J. Biol. Chem., (1993), vol. 268, No. 35, pp. 26033-26036.
"Bessatsu-Igaku no Ayumi (Supplementary volume Journal of Clinical and Experimental Medicine), Renal disease state of arts 2003-2005, Ishiyaku Publishers, Inc." (extract plus p. 216).
Y. Sado et al., "Expression of Collagen IV Genes and Goodpasture Antigens", In Extra Cellular Matrix-Cellular Interaction: Molecules to Diseases, ed by Ninomiya Y et al. Japan Sci Soc. Press, Tokyo/S Karger, Basel. 1998, pp. 235-260.
Dehan P. et al., Identification of post-transplant anti-alpha 5 (IV) collagen alloantibodies in X-linked Alport syndrome, Nephrol. Dial. Transplant., 1996, vol. 11, No. 10, pp. 1983-1988.
Satoshi Hino, "IV Collagen alpha 5-sa no Seijo Soshiki Bunpu to Alport Shokogun de no Ijo", Medical Journal of Kinki University, 1995, vol. 20, No. 1, pp. 59-69, English Abstract.
International Search Report in corresponding application PCT/JP2007/061779 dated Jul. 10, 2007.
Tsukao Yokoyama et al., "Nyo to Kessei ni Okeru NC1 (Type IV Collagen NC1 Ryoiki) to Ko NC1 Kotai no Sokutei", The Cell, 2003, vol. 35, No. 4, pp. 150-154.
Tsukao Yokoyama et al., "Type IV Collagen NC1 Ryoiki NC1 Ryoiki (NC1)) ni Taisuru Monoclonal Kotai (12D) no Tokusei", The Journal of Medicine, 2005, vol. 53, No. 3, pp. 335-41.
Tsukao Yokoyama et al., "Jin' ennyo wa Type IV Collagen alpha 5-sa NC1 Jo no Doitsu peptide Hairetsu o Ninshiki suru", The Journal of Medicine, May 2007, vol. 57, No. 5, pp. 605-13.
Tsukao Yokoyama et al., "Shikyutai Jin' en no Futatsu no. Shihyo", The Journal of Medicine, 2004, vol. 51, No. 4, pp. 567-72.

(Continued)

*Primary Examiner* — Maher Haddad
(74) *Attorney, Agent, or Firm* — Sughrue Mion, PLLC

(57) ABSTRACT

A type IV collagen-like immunoreactive peptide and an antibody thereof which are useful for detecting nephritis, a method for selecting a type IV collagen-like immunoreactive peptide, a method for screening an immunoreactive antibody and an immunoreactive peptide, a nephritis model, a method for detecting chronic nephritis, a vaccine, and a therapeutic agent for nephritis are provided.

A type IV collagen-like immunoreactive peptide immunologically reacts with an isolated, chronic nephritis-derived biological sample. Preferably, the type IV collagen-like immunoreactive peptide includes at least one member selected from the group consisting of at least one chain selected from alpha 1 to alpha 6 chains as a constituent alpha chain, at least one region selected from 7S, the central helical domain, and NC1 as a constituent region, and a peptide having 3 to 35 amino acids as a constituent peptide.

3 Claims, 6 Drawing Sheets

OTHER PUBLICATIONS

Tsukao Yokoyama et al., "Ko type IV Collagen NC1 Ryoiki (NC1) Kotai wa Hiroi Han' i no. Jin' ennyo Chu ni Kenshutsu Sareru", The Journal of Medicine, 2005, vol. 53, No. 3, pp. 343-6.

Tsukao Yokoyama et al., "Type IV Collagen no NC1 Ryoiki (K35) ni yori Yudo sareru Jin' en Model", The Cell, 2002, vol. 34, No. 4, pp. 182-5.

* cited by examiner

FIG.4

|  | REAL NUMBER | REAL NUMBER | LATERAL Ave. | STANDARD DEVIATION | CV |
|---|---|---|---|---|---|
| <STANDARD> | | | | | |
| S0 | 0.078 | 0.072 | 0.075 | 0.004 | 5.657 |
| S2 | 0.250 | 0.232 | 0.241 | 0.013 | 5.281 |
| S3 | 0.381 | 0.383 | 0.382 | 0.001 | 0.370 |
| S4 | 0.689 | 0.632 | 0.661 | 0.040 | 6.102 |
| S5 | 1.142 | 1.093 | 1.118 | 0.035 | 3.101 |
| S6 | 2.012 | 2.067 | 2.040 | 0.039 | 1.907 |
| <CONTROL> | | | | | |
| D2 | 0.539 | 0.561 | 0.550 | 0.016 | 2.828 |
| Y | 0.546 | 0.520 | 0.533 | 0.018 | 3.449 |
| <GBM STANDARD> | | | | | |
| C(*2) | 2.745 | 2.656 | 2.701 | 0.063 | 2.330 |
| D(*2) | 0.853 | 0.785 | 0.819 | 0.048 | 5.871 |
| E(−)(*2) | 0.206 | 0.199 | 0.203 | 0.005 | 2.444 |
| TD31 | 0.216 | 0.167 | 0.192 | 0.035 | 18.093 |
| TD32 | 0.219 | 0.220 | 0.220 | 0.001 | 0.322 |
| TD33 | 0.198 | 0.198 | 0.198 | 0.000 | 0.000 |
| TD34 | 0.255 | 0.248 | 0.252 | 0.005 | 1.968 |
| TD35 | 0.314 | 0.324 | 0.319 | 0.007 | 2.217 |
| TD36 | 0.319 | 0.276 | 0.298 | 0.030 | 10.220 |
| TD37 | 0.401 | 0.380 | 0.391 | 0.015 | 3.803 |
| TD38 | 1.059 | 0.957 | 1.008 | 0.072 | 7.155 |
| TD39 | 0.139 | 0.139 | 0.139 | 0.000 | 0.000 |
| TD40 | 0.149 | 0.137 | 0.143 | 0.008 | 5.934 |
| TD41 | 0.408 | 0.393 | 0.401 | 0.011 | 2.648 |
| TD42 | 2.728 | 2.664 | 2.696 | 0.045 | 1.679 |

FIG.5

HUMAN IV α3 NC1
PATWTTRGFVFTRHSQTTAIPSCPEGTVPLYSGFSFLFVQGNQRAHGQDLGTLGS
CLQRFTTMPFLFCNVNDVCNFASRNDYSYWLSTPALMPMNMAPITGRALEPYISR
CTVCEGPAIAIAVHSQTTDIPPCPHGWISLWKGFSFIMFTSAGSEGTGQALASPGS
CLEEFRASPFLECHGRGTCNYYSNSYSFWLASLNPERMFRKPIPSTVKAGELEKIIS
RCQVCMKKRH

HUMAN IV α4 NC1
GPGYLGGFLLVLHSQTDQEPTCPLGMPRLWTGYSLLYLEGQEKAHNQDLGLAGS
CLPVFSTLPFAYCNIHQVCHYAQRNDRSYWLASAAPLPMMPLSEEAIRPYVSRCA
VCEAPAQAVAVHSQDQSIPPCPQTWRSLWIGYSFLMHTGAGDQGGGQALMSPG
SCLEDFRAAPFLECQGRQGTCHFFANKYSFWLTTVKADLQFSSAPAPDTLKESQ
AQRQKISRCQVCVKYS

HUMAN IV α5 NC1
GTSSVAHGFLITRHSQTTDAPQCPQGTLQVYEGFSLLYVQGNKRAHGQDLGTAG
SCLRRFSTMPFMFCNINNVCNFASRNDYSYWLSTPEPMPMSMQPLKGQSIQPFISR
CAVCEAPAVVIAVHSQTIQIPHCPQGWDSLWIGYSFMMHTSAGAEGSGQALASP
GSCLEEFRSAPFIECHGRGTCNYYANSYSFWLATVDVSDMFSKPQSETLKAGDLR
TRISRCQVCMKRT

HUMAN IV α6 NC1
GQSMRVGYTLVKHSQSEQVPPCPIGMSQLWVGYSLLFVEGQEKAHNQDLGFAGS
CLPRFSTMPFIYCNINEVCHYARRNDKSYWLSTTAPIPMMPVSQTQIPQYISRCSVC
EAPSQAIAVHSQDITIPQCPLGWRSLWIGYSFLMHTAAGAEGGGQSLVSPGSCLE
DFRATPFIECSGARGTCHYFANKYSFWLTTVEERQQFGELPVSETLKAGQLHTRV
SRCQVCMKSL

FIG.6

| TD31 31 | Abs. | | Average |
|---|---|---|---|
| H4NA5-1 | 0.080 | 0.051 | 0.066 |
| H4NA5-2 | 0.083 | 0.051 | 0.067 |
| H4NA5-3 | 0.053 | 0.098 | 0.076 |
| H4NA5-4 | 0.098 | 0.090 | 0.094 |
| H4NA5-5 | 0.112 | 0.090 | 0.101 |
| H4NA5-6 | 0.065 | 0.100 | 0.083 |
| H4NA5-7 | 0.141 | 0.077 | 0.109 |
| H4NA5-8 | 0.164 | 0.117 | 0.141 |
| H4NA5-9 | 0.215 | 0.083 | 0.149 |
| H4NA5-10 | 0.059 | 0.488 | 0.274 |
| H4NA5-11 | 0.329 | 0.078 | 0.204 |
| H4NA5-12 | 0.287 | 0.053 | 0.170 |
| H4NA5-13 | 0.077 | 0.064 | 0.071 |
| H4NA5-14 | 0.150 | 0.067 | 0.109 |
| H4NA5-15 | 0.060 | 0.054 | 0.057 |
| H4NA3-1 | 0.141 | 0.063 | 0.102 |

| TD32 32 | Abs. | | Average |
|---|---|---|---|
| H4NA5-1 | 0.082 | 0.079 | 0.081 |
| H4NA5-2 | 0.096 | 0.068 | 0.082 |
| H4NA5-3 | 0.076 | 0.071 | 0.074 |
| H4NA5-4 | 0.074 | 0.087 | 0.081 |
| H4NA5-5 | 0.142 | 0.130 | 0.136 |
| H4NA5-6 | 0.082 | 0.122 | 0.102 |
| H4NA5-7 | 0.114 | 0.066 | 0.090 |
| H4NA5-8 | 0.140 | 0.154 | 0.147 |
| H4NA5-9 | 0.073 | 0.085 | 0.079 |
| H4NA5-10 | 0.111 | 0.086 | 0.099 |
| H4NA5-11 | 0.123 | 0.081 | 0.102 |
| H4NA5-12 | 0.078 | 0.100 | 0.089 |
| H4NA5-13 | 0.123 | 0.092 | 0.108 |
| H4NA5-14 | 0.100 | 0.072 | 0.086 |
| H4NA5-15 | 0.095 | 0.103 | 0.099 |
| H4NA3-1 | 0.191 | 0.157 | 0.174 |

| TD38 38 | Abs. | | Average |
|---|---|---|---|
| H4NA5-1 | 0.347 | 0.178 | 0.263 |
| H4NA5-2 | 0.257 | 0.251 | 0.254 |
| H4NA5-3 | 0.284 | 0.388 | 0.336 |
| H4NA5-4 | 0.255 | 0.217 | 0.236 |
| H4NA5-5 | 0.642 | 0.635 | 0.639 |
| H4NA5-6 | 0.255 | 0.190 | 0.223 |
| H4NA5-7 | 0.256 | 0.193 | 0.225 |
| H4NA5-8 | 0.511 | 0.619 | 0.565 |
| H4NA5-9 | 0.168 | 0.232 | 0.200 |
| H4NA5-10 | 0.437 | 0.402 | 0.420 |
| H4NA5-11 | 0.176 | 0.195 | 0.186 |
| H4NA5-12 | 0.355 | 0.370 | 0.363 |
| H4NA5-13 | 0.457 | 0.384 | 0.421 |
| H4NA5-14 | 0.200 | 0.142 | 0.171 |
| H4NA5-15 | 0.305 | 0.369 | 0.337 |
| H4NA3-1 | 0.290 | 0.313 | 0.302 |

| TD42 42 | Abs. | | Average |
|---|---|---|---|
| H4NA5-1 | 0.496 | 0.275 | 0.386 |
| H4NA5-2 | 0.257 | 0.251 | 0.254 |
| H4NA5-3 | 0.284 | 0.388 | 0.336 |
| H4NA5-4 | 0.465 | 0.638 | 0.552 |
| H4NA5-5 | 1.703 | 1.829 | 1.766 |
| H4NA5-6 | 0.253 | 0.280 | 0.267 |
| H4NA5-7 | 0.356 | 0.410 | 0.383 |
| H4NA5-8 | 2.076 | 2.083 | 2.080 |
| H4NA5-9 | 0.195 | 0.281 | 0.238 |
| H4NA5-10 | 2.026 | 2.157 | 2.092 |
| H4NA5-11 | 0.272 | 0.296 | 0.284 |
| H4NA5-12 | 0.946 | 1.011 | 0.979 |
| H4NA5-13 | 2.423 | 1.753 | 2.088 |
| H4NA5-14 | 0.232 | 0.226 | 0.229 |
| H4NA5-15 | 0.441 | 0.494 | 0.468 |
| H4NA3-1 | 0.433 | 0.354 | 0.394 |

| TD33 33 | Abs. | | Average |
|---|---|---|---|
| H4NA5-1 | 0.073 | 0.066 | 0.070 |
| H4NA5-2 | 0.063 | 0.059 | 0.061 |
| H4NA5-3 | 0.062 | 0.074 | 0.068 |
| H4NA5-4 | 0.078 | 0.069 | 0.074 |
| H4NA5-5 | 0.126 | 0.079 | 0.103 |
| H4NA5-6 | 0.102 | 0.166 | 0.134 |
| H4NA5-7 | 0.340 | 0.186 | 0.263 |
| H4NA5-8 | 0.108 | 0.102 | 0.105 |
| H4NA5-9 | 0.054 | 0.189 | 0.122 |
| H4NA5-10 | 0.121 | 0.113 | 0.117 |
| H4NA5-11 | 0.064 | 0.062 | 0.063 |
| H4NA5-12 | 0.074 | 0.071 | 0.073 |
| H4NA5-13 | 0.081 | 0.074 | 0.078 |
| H4NA5-14 | 0.092 | 0.068 | 0.080 |
| H4NA5-15 | 0.468 | 0.494 | 0.481 |
| H4NA3-1 | 0.192 | 0.167 | 0.180 |

| IgA | Abs. | | Average |
|---|---|---|---|
| H4NA5-1 | 0.467 | 0.342 | 0.405 |
| H4NA5-2 | 0.350 | 0.387 | 0.369 |
| H4NA5-3 | 0.393 | 0.400 | 0.397 |
| H4NA5-4 | 0.619 | 0.606 | 0.613 |
| H4NA5-5 | 2.347 | 2.364 | 2.356 |
| H4NA5-6 | 0.308 | 0.244 | 0.276 |
| H4NA5-7 | 0.670 | 0.503 | 0.587 |
| H4NA5-8 | 2.794 | 2.736 | 2.765 |
| H4NA5-9 | 0.363 | 0.475 | 0.419 |
| H4NA5-10 | 2.250 | 2.272 | 2.261 |
| H4NA5-11 | 0.451 | 0.388 | 0.420 |
| H4NA5-12 | 1.828 | 1.887 | 1.858 |
| H4NA5-13 | 2.105 | 2.114 | 2.110 |
| H4NA5-14 | 0.278 | 0.229 | 0.254 |
| H4NA5-15 | 0.468 | 0.494 | 0.481 |
| H4NA3-1 | 0.734 | 0.600 | 0.667 | ly as to the

SEQUENCE LISTING

<160> NUMBER OF SEQ ID NOS: 9

<210> SEQ ID NO 1
<211> LENGTH: 233
<212> TYPE: PRT
<213> ORGANISM: Homo sapiens

<400> SEQUENCE: 1

Pro Ala Thr Trp Thr Thr Arg Gly Phe Val Phe Thr Arg His Ser Gln
1               5                   10                  15

Thr Thr Ala Ile Pro Ser Cys Pro Glu Gly Thr Val Pro Leu Tyr Ser
            20                  25                  30

Gly Phe Ser Phe Leu Phe Val Gln Gly Asn Gln Arg Ala His Gly Gln
        35                  40                  45

Asp Leu Gly Thr Leu Gly Ser Cys Leu Gln Arg Phe Thr Thr Met Pro
    50                  55                  60

Phe Leu Phe Cys Asn Val Asn Asp Val Cys Asn Phe Ala Ser Arg Asn
65                  70                  75                  80

Asp Tyr Ser Tyr Trp Leu Ser Thr Pro Ala Leu Met Pro Met Asn Met
                85                  90                  95

Ala Pro Ile Thr Gly Arg Ala Leu Glu Pro Tyr Ile Ser Arg Cys Thr
            100                 105                 110

Val Cys Glu Gly Pro Ala Ile Ala Ile Ala Val His Ser Gln Thr Thr
        115                 120                 125

Asp Ile Pro Pro Cys Pro His Gly Trp Ile Ser Leu Trp Lys Gly Phe
    130                 135                 140

Ser Phe Ile Met Phe Thr Ser Ala Gly Ser Glu Gly Thr Gly Gln Ala
145                 150                 155                 160

Leu Ala Ser Pro Gly Ser Cys Leu Glu Glu Phe Arg Ala Ser Pro Phe
                165                 170                 175

Leu Glu Cys His Gly Arg Gly Thr Cys Asn Tyr Tyr Ser Asn Ser Tyr
            180                 185                 190

Ser Phe Trp Leu Ala Ser Leu Asn Pro Glu Arg Met Phe Arg Lys Pro
        195                 200                 205

Ile Pro Ser Thr Val Lys Ala Gly Glu Leu Glu Lys Ile Ile Ser Arg
    210                 215                 220

Cys Gln Val Cys Met Lys Lys Arg His
225                 230

<210> SEQ ID NO 2
<211> LENGTH: 232
<212> TYPE: PRT
<213> ORGANISM: Homo sapiens

<400> SEQUENCE: 2

Gly Pro Gly Tyr Leu Gly Phe Leu Leu Val Leu His Ser Gln Thr
1               5                   10                  15

Asp Gln Glu Pro Thr Cys Pro Leu Gly Met Pro Arg Leu Trp Thr Gly
            20                  25                  30

Tyr Ser Leu Leu Tyr Leu Glu Gly Gln Glu Lys Ala His Asn Gln Asp
        35                  40                  45

Leu Gly Leu Ala Gly Ser Cys Leu Pro Val Phe Ser Thr Leu Pro Phe
    50                  55                  60

Ala Tyr Cys Asn Ile His Gln Val Cys His Tyr Ala Gln Arg Asn Asp
65                  70                  75                  80

```
Arg Ser Tyr Trp Leu Ala Ser Ala Ala Pro Leu Pro Met Met Pro Leu
             85                  90                  95

Ser Glu Glu Ala Ile Arg Pro Tyr Val Ser Arg Cys Ala Val Cys Glu
            100                 105                 110

Ala Pro Ala Gln Ala Val Ala Val His Ser Gln Asp Gln Ser Ile Pro
            115                 120                 125

Pro Cys Pro Gln Thr Trp Arg Ser Leu Trp Ile Gly Tyr Ser Phe Leu
            130                 135                 140

Met His Thr Gly Ala Gly Asp Gln Gly Gly Gln Ala Leu Met Ser
145                 150                 155                 160

Pro Gly Ser Cys Leu Glu Asp Phe Arg Ala Ala Pro Phe Leu Glu Cys
            165                 170                 175

Gln Gly Arg Gln Gly Thr Cys His Phe Phe Ala Asn Lys Tyr Ser Phe
            180                 185                 190

Trp Leu Thr Thr Val Lys Ala Asp Leu Gln Phe Ser Ser Ala Pro Ala
            195                 200                 205

Pro Asp Thr Leu Lys Glu Ser Gln Ala Gln Arg Gln Lys Ile Ser Arg
            210                 215                 220

Cys Gln Val Cys Val Lys Tyr Ser
225                 230

<210> SEQ ID NO 3
<211> LENGTH: 232
<212> TYPE: PRT
<213> ORGANISM: Homo sapiens

<400> SEQUENCE: 3

Gly Thr Ser Ser Val Ala His Gly Phe Leu Ile Thr Arg His Ser Gln
1               5                   10                  15

Thr Thr Asp Ala Pro Gln Cys Pro Gln Gly Thr Leu Gln Val Tyr Glu
             20                  25                  30

Gly Phe Ser Leu Leu Tyr Val Gln Gly Asn Lys Arg Ala His Gly Gln
            35                  40                  45

Asp Leu Gly Thr Ala Gly Ser Cys Leu Arg Arg Phe Ser Thr Met Pro
50                  55                  60

Phe Met Phe Cys Asn Ile Asn Asn Val Cys Asn Phe Ala Ser Arg Asn
65                  70                  75                  80

Asp Tyr Ser Tyr Trp Leu Ser Thr Pro Glu Pro Met Pro Met Ser Met
             85                  90                  95

Gln Pro Leu Lys Gly Gln Ser Ile Gln Pro Phe Ile Ser Arg Cys Ala
            100                 105                 110

Val Cys Glu Ala Pro Ala Val Val Ile Ala Val His Ser Gln Thr Ile
            115                 120                 125

Gln Ile Pro His Cys Pro Gln Gly Trp Asp Ser Leu Trp Ile Gly Tyr
            130                 135                 140

Ser Phe Met Met His Thr Ser Ala Gly Ala Glu Gly Ser Gly Gln Ala
145                 150                 155                 160

Leu Ala Ser Pro Gly Ser Cys Leu Glu Glu Phe Arg Ser Ala Pro Phe
            165                 170                 175

Ile Glu Cys His Gly Arg Gly Thr Cys Asn Tyr Tyr Ala Asn Ser Tyr
            180                 185                 190

Ser Phe Trp Leu Ala Thr Val Asp Val Ser Asp Met Phe Ser Lys Pro
            195                 200                 205

Gln Ser Glu Thr Leu Lys Ala Gly Asp Leu Arg Thr Arg Ile Ser Arg
            210                 215                 220
```

```
Cys Gln Val Cys Met Lys Arg Thr
225                 230
```

<210> SEQ ID NO 4
<211> LENGTH: 231
<212> TYPE: PRT
<213> ORGANISM: Homo sapiens

<400> SEQUENCE: 4

```
Gly Gln Ser Met Arg Val Gly Tyr Thr Leu Val Lys His Ser Gln Ser
1               5                   10                  15

Glu Gln Val Pro Pro Cys Pro Ile Gly Met Ser Gln Leu Trp Val Gly
            20                  25                  30

Tyr Ser Leu Leu Phe Val Glu Gly Gln Glu Lys Ala His Asn Gln Asp
        35                  40                  45

Leu Gly Phe Ala Gly Ser Cys Leu Pro Arg Phe Ser Thr Met Pro Phe
    50                  55                  60

Ile Tyr Cys Asn Ile Asn Glu Val Cys His Tyr Ala Arg Arg Asn Asp
65                  70                  75                  80

Lys Ser Tyr Trp Leu Ser Thr Thr Ala Pro Ile Pro Met Met Pro Val
                85                  90                  95

Ser Gln Thr Gln Ile Pro Gln Tyr Ile Ser Arg Cys Ser Val Cys Glu
            100                 105                 110

Ala Pro Ser Gln Ala Ile Ala Val His Ser Gln Asp Ile Thr Ile Pro
        115                 120                 125

Gln Cys Pro Leu Gly Trp Arg Ser Leu Trp Ile Gly Tyr Ser Phe Leu
    130                 135                 140

Met His Thr Ala Ala Gly Ala Glu Gly Gly Gly Gln Ser Leu Val Ser
145                 150                 155                 160

Pro Gly Ser Cys Leu Glu Asp Phe Arg Ala Thr Pro Phe Ile Glu Cys
                165                 170                 175

Ser Gly Ala Arg Gly Thr Cys His Tyr Phe Ala Asn Lys Tyr Ser Phe
            180                 185                 190

Trp Leu Thr Thr Val Glu Glu Arg Gln Gln Phe Gly Glu Leu Pro Val
        195                 200                 205

Ser Glu Thr Leu Lys Ala Gly Gln Leu His Thr Arg Val Ser Arg Cys
    210                 215                 220

Gln Val Cys Met Lys Ser Leu
225                 230
```

<210> SEQ ID NO 5
<211> LENGTH: 20
<212> TYPE: PRT
<213> ORGANISM: Artificial Sequence
<220> FEATURE:
<223> OTHER INFORMATION: peptide with homology to Type IV collagen

<400> SEQUENCE: 5

```
Gly Arg Gly Thr Cys Asn Tyr Tyr Ala Asn Ser Tyr Ser Phe Trp Leu
1               5                   10                  15

Ala Thr Val Asp
            20
```

<210> SEQ ID NO 6
<211> LENGTH: 20
<212> TYPE: PRT
<213> ORGANISM: Artificial Sequence
<220> FEATURE:
<223> OTHER INFORMATION: peptide with homology to Type IV collagen

```
-continued

<400> SEQUENCE: 6

Ser Cys Leu Glu Glu Phe Arg Ser Ala Pro Phe Ile Glu Cys His Gly
1               5                   10                  15

Arg Gly Thr Cys
            20

<210> SEQ ID NO 7
<211> LENGTH: 20
<212> TYPE: PRT
<213> ORGANISM: Artificial Sequence
<220> FEATURE:
<223> OTHER INFORMATION: peptide with homology to Type IV collagen

<400> SEQUENCE: 7

Gly Trp Asp Ser Leu Trp Ile Gly Tyr Ser Phe Met Met His Thr Ser
1               5                   10                  15

Ala Gly Ala Glu
            20

<210> SEQ ID NO 8
<211> LENGTH: 20
<212> TYPE: PRT
<213> ORGANISM: Artificial Sequence
<220> FEATURE:
<223> OTHER INFORMATION: peptide with homology to Type IV collagen

<400> SEQUENCE: 8

Pro Phe Ile Ser Arg Cys Ala Val Cys Glu Ala Pro Ala Val Val Ile
1               5                   10                  15

Ala Val His Ser
            20

<210> SEQ ID NO 9
<211> LENGTH: 20
<212> TYPE: PRT
<213> ORGANISM: Artificial Sequence
<220> FEATURE:
<223> OTHER INFORMATION: peptide with homology to Type IV collagen

<400> SEQUENCE: 9

Ser Thr Met Pro Phe Met Phe Cys Asn Ile Asn Asn Val Cys Asn Phe
1               5                   10                  15

Ala Ser Arg Asn
            20
```

TYPE IV COLLAGEN-LIKE IMMUNOREACTIVE PEPTIDE

TECHNICAL FIELD

The present invention relates to a type IV collagen-like immunoreactive peptide, an antibody thereof, a method for selecting a type IV collagen-like immunoreactive peptide, a method for screening an immunoreactive antibody or an immunoreactive peptide, a nephritis model, a method for detecting chronic nephritis, a vaccine, and a therapeutic agent for nephritis.

BACKGROUND ART

Type IV collagen has not yet been fully elucidated. Many molecules of type IV collagen are bound to each other and, in association with various components, form tissue basement membranes. Furthermore, type IV collagen is a major component of tissue basement membranes, and thus is also referred to as "basement membrane collagen". Type IV collagen has six isomers: alpha 1 to alpha 6 chains, and one molecule of type IV collagen is composed of three alpha chains. The combination of three alpha chains varies depending on the tissue. Alpha 1 and alpha 2 chains occur in abundance in basement membranes derived from placenta, which are commonly found in the tissue basement membranes throughout the body. Basement membranes derived from kidneys have specificity and alpha 3 to alpha 6 chains are said to occur in abundance therein.

One molecule of type IV collagen is divided into three domains: the 7S domain located at the N-terminus and the central helical domain (TH), each having a triple-helical structure, and the NC1 domain having a non-helical structure located in the C-terminus region. When type IV collagen is extracted from the tissue of a living body, the domains obtained differ depending on the treatment method. In general techniques, triple-helical domains are obtained by pepsin treatment and NC1 is obtained by bacteria-derived collagenase treatment (Non-Patent Document 1).

Meanwhile, nephritis is broadly classified into "acute nephritis" and "chronic nephritis", on the basis of symptoms, which are subclassified and variously named by specialists. Since nephritis usually refers to "chronic nephritis", in the present invention, "nephritis" and "chronic nephritis" are used synonymously unless otherwise stated. Examples of "chronic nephritis" include, but are not limited to, so-called chronic nephritis, IgA nephropathy, minimal-change nephrosis, membranous nephropathy, and secondary nephropathy, such as diabetic nephropathy and hypertensive nephropathy. With respect to nephritis, 30,000 patients are newly introduced to dialysis every year, which causes a tremendous burden on the quality of life (QOL) of patients as well as to the national medical expenses (6,000,000 yen/year for each dialysis case). Although dialysis techniques are advancing, there are currently no pharmaceutical agents for treating nephritis directly by identifying nephropathy in the very early stage before dialysis is required. The major reason for this is that the mechanism of onset of nephritis has not yet been elucidated.

Furthermore, under the assumption that there exist antigens specific to nephritis, various antigen substances are currently under study around the world (Non-Patent Document 2). If antigens are identified, development of diagnostic agents or therapeutic agents for nephritis is expected, using the antigens as target substances. Goodpasture syndrome (anti-glomerular basement membrane (GBM) antibody nephritis in a narrow sense) is only one example in which antigens have been determined. It has been reported that the antigens are localized to 36 amino acid residues at the C-terminus of NC1 of the alpha 3 chain, and the amino acid sequences, from the N-terminus, 17 to 31 and 127 to 141 of the alpha 3 chain (Non-Patent Document 3). Each of the antigens is located on the alpha 3 chain. Furthermore, locations of 17 to 31 (15 amino acid residues) and 127 to 141 (15 amino acid residues) on the alpha 3 chain are being searched for from the chimera alpha 1/alpha 3 NC1.

Goodpasture syndrome, which is rare nephritis, belongs to "acute nephritis", and typically, a serious condition occurs in about two weeks. Thus, a definite diagnosis must be immediately established. In order to establish the definite diagnosis, immunostaining of kidney biopsies is performed, and determination is made on the basis of the presence or absence of deposition of immunoglobulin IgG, which is an autoantibody to GBM.

Non-Patent Document 1: Extracellular Matrix IRL PRESS/ OXFORD UNIVERSITY PRESS Oxford N.Y.
Non-Patent Document 2: Jin To Toseki (Kidney And Dialysis) 2005 July vol. 59 No. 1, Tokyo Igakusha
Non-Patent Document 3: J. Biol Chem (1993) 268, 26033-26036

DISCLOSURE OF INVENTION

Problems to be Solved by the Invention

However, in such an examination, specimen collection may cause pain and risk to patients, and immunostaining requires pathology specialists to have high diagnostic capability, all of which are problems.

Under these circumstances, as a simple method, ELISA kits (trade name: Nephroscholar-GBM, imported by Nissho Corp., sold by Nipro Corp.) which detect autoantibodies appearing in blood are used. However, according to the instruction book included with the ELISA kits and the document (Rinshokiki-Shiyaku (Clinical equipment-reagent), Vol. 20 No. 3, 367-374 (1997)) cited therein, autoantibodies of Goodpasture syndrome are only detected when they exist in high concentrations, and other types of nephritis are only detected when they exist in low concentrations, which are substantially the same as those of healthy subjects. According to the instruction book, the antigens used are bovine GBM antigens. The GBM is composed of various components including type IV collagen as a major component. In terms of size, the relationship is as follows: GBM>type IV collagen>NC1>NC1 of alpha 3 chain>the amino acid residues (antigens) described above. Use of bovine GBMs as antigens means that there are no antigens of other types of nephritis in this huge region, which is insufficient for detecting nephritis. Furthermore, the ELISA kits are approved only as diagnostic agents and covered by the national health insurance in Japan, but are difficult to use because they are expensive and imported products.

Accordingly, it is an object of the present invention to provide a type IV collagen-like immunoreactive peptide and an antibody thereof which are useful for detecting nephritis, a method for selecting a type IV collagen-like immunoreactive peptide, a method for screening an immunoreactive antibody and an immunoreactive peptide, a nephritis model, a method for detecting chronic nephritis, a vaccine, and a therapeutic agent for nephritis.

Means for Solving the Problems

In order to solve the problems described above, the present inventor has conducted diligent studies for a long time on development of therapeutic agents for renal diseases and secondary renal diseases associated with other diseases and methods for early detection thereof. As a result, antigenic sites in nephritis have been found, using a chronic nephritis-derived biological sample, and a type IV collagen-like immunoreactive peptide and an antibody thereof, a method for selecting a type IV collagen-like immunoreactive peptide, a method for screening an immunoreactive antibody and an immunoreactive peptide, a nephritis model, a method for detecting chronic nephritis, a vaccine, and a therapeutic agent for nephritis have been established, thus completing the present invention.

That is, a type IV collagen-like immunoreactive peptide of the present invention is characterized in that it immunologically reacts with an isolated, chronic nephritis-derived biological sample.

Furthermore, an antibody of a type IV collagen-like immunoreactive peptide of the present invention is characterized in that it immunologically reacts with the type IV collagen-like immunoreactive peptide.

Furthermore, a method for selecting a type IV collagen-like immunoreactive peptide of the present invention is characterized in that, by using an isolated, chronic nephritis-derived biological sample as a ligand, the type IV collagen-like immunoreactive peptide which immunologically reacts with the chronic nephritis-derived biological sample is selected.

Furthermore, a method for screening an immunoreactive antibody of the present invention is characterized in that it uses the type IV collagen-like immunoreactive peptide.

Furthermore, a method for screening an immunoreactive peptide of the present invention is characterized in that it uses the antibody of the type IV collagen-like immunoreactive peptide.

Furthermore, a nephritis model of the present invention is characterized in that it uses, as an inducer, at least one of the type IV collagen-like immunoreactive peptide and the antibody of the type IV collagen-like immunoreactive peptide.

Furthermore, a method for detecting chronic nephritis of the present invention is characterized in that it uses at least one of the type IV collagen-like immunoreactive peptide and the antibody of the type IV collagen-like immunoreactive peptide.

Furthermore, a vaccine of the present invention is characterized in that it uses at least one member selected from the group consisting of the type IV collagen-like immunoreactive peptide and the antibody of the type IV collagen-like immunoreactive peptide. Furthermore, a therapeutic agent for nephritis is characterized in that it contains the vaccine.

Advantages

The present invention can provide a type IV collagen-like immunoreactive peptide and an antibody thereof which are useful for detecting nephritis, a method for selecting a type IV collagen-like immunoreactive peptide, a method for screening an immunoreactive antibody and an immunoreactive peptide, a nephritis model, a method for detecting chronic nephritis, a vaccine, and a therapeutic agent for nephritis.

BRIEF DESCRIPTION OF DRAWINGS

FIG. 4 shows the comparison of measured data (anti-NC1 antibody) with respect to chronic nephritis TD38, diabetic nephritis TD42, and healthy subjects (TD31 to 37 and TD39 to 41).

FIG. 5 shows the alpha 3 chain (SEQ ID NO: 1), alpha 4 chain (SEQ ID NO: 2), alpha 5 chain (SEQ ID NO: 3), and alpha 6 chain (SEQ ID NO: 4) of human NC1.

FIG. 6 shows the comparison with respect to NC1-like antigenicity among chronic nephritis No. 38, diabetic nephritis No. 42, IgA nephropathy, and healthy subjects Nos. 31, 32, and 33.

BEST MODES FOR CARRYING OUT THE INVENTION

Figure 1:
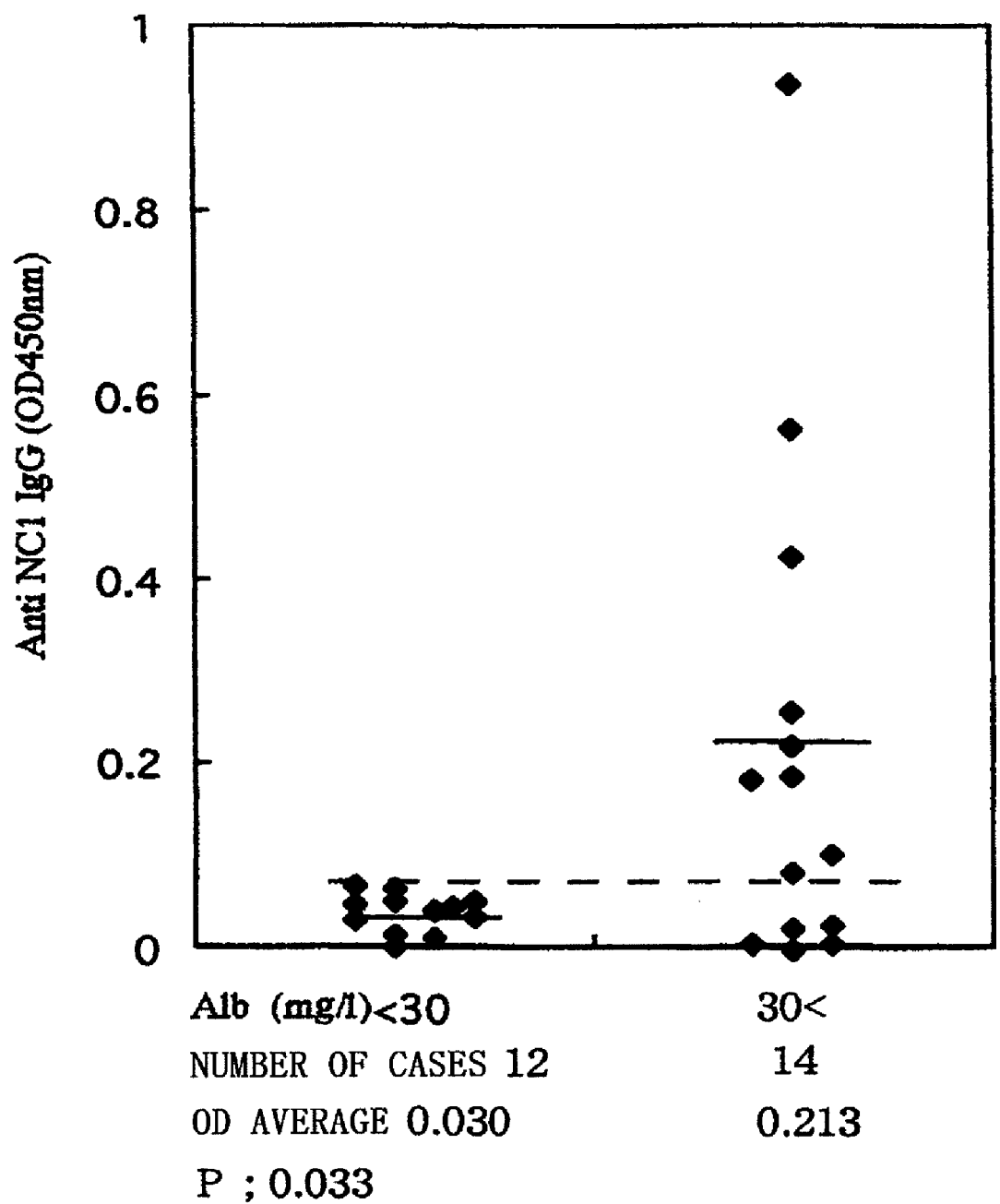
FIG. 1 is a graph showing the comparison (anti-NC1 antibody) between healthy subjects and persons with high urinary albumin level.

A type IV collagen-like immunoreactive peptide of the present invention will be described below.

A type IV collagen-like immunoreactive peptide of the present invention is characterized in that it immunologically reacts with an isolated, chronic nephritis-derived biological sample. This is an immunoreaction in which the type IV collagen-like immunoreactive peptide acts as an antigen and the isolated, chronic nephritis-derived biological sample acts as an antibody. The immunoreaction is not limited to an enzyme immunoreaction. Examples of the immunoreaction also include an AB method, RIA, an immunoluminescence method, a precipitation reaction, and an agglutination reaction and the like. As an enzyme-labeled antibody, either a polyclonal or monoclonal antibody may be used. The antibody may be radiolabeled, luminescence-labeled, or non-labeled. The reaction mode is not limited to a sandwich method, but a competitive method or the like may be used. Glass, a magnetic substance, or a latex may be used instead of a plate. Alternatively, without using any of these, the solid phase method may not be employed.

Furthermore, in the present invention, examples of "chronic nephritis" include, but are not limited to, so-called chronic nephritis, IgA nephropathy, minimal-change nephrosis, membranous nephropathy, and secondary nephropathy, such as diabetic nephropathy and hypertensive nephropathy.

Furthermore, the type IV collagen-like immunoreactive peptide of the present invention is not particularly limited as long as it immunologically reacts with the chronic nephritis-derived biological sample. Preferably, the type IV collagen-like immunoreactive peptide includes at least one member selected from the group consisting of at least one chain selected from alpha 1 to alpha 6 chains as a constituent alpha chain, at least one region selected from 7S, the central helical domain, and NC1 as a constituent region, and a peptide having 3 to 35 amino acids as a constituent peptide. More preferably, the type IV collagen-like immunoreactive peptide includes the alpha 5 chain, and the constituent region is more preferably NC1. Furthermore, the peptide length of such a type IV collagen-like immunoreactive peptide is preferably 3 to 35 amino acids in view of cost and efficiency, and most preferably 10 to 20 amino acids in view of also achieving ease of production of the antibody.

The type IV collagen-like immunoreactive peptide of the present invention immunologically reacts with an isolated, chronic nephritis-derived biological sample in the same manner as type IV collagen. Furthermore, the type IV collagen-like immunoreactive peptide is preferably homologous to the amino acid sequence of the alpha 5 chain of the type IV collagen.

The type IV collagen-like immunoreactive peptide of the present invention preferably includes at least one amino acid sequence, derived from NC1 as the constituent region, selected from the group consisting of:
1) GRGTC NYYAN SYSFW LATVD (SEQ ID NO: 5) NO. yp13
2) SCLEE FRSAP FIECH GRGTC (SEQ ID NO: 6) NO. yp12
3) GWDSL WIGYS FMMHT SAGAE (SEQ ID NO: 7) NO. yp10
4) PFISR CAVCE APAVV IAVHS (SEQ ID NO: 8) NO. yp08
5) STMPF MFCNI NNVCN FASRN (SEQ ID NO: 9) NO. yp05
(wherein a represents alanine, C represents cysteine, D represents aspartic acid, E represents glutamic acid, F represents phenylalanine, G represents glycine, H represents histidine, I represents isoleucine, L represents leucine, M represents methionine, N represents asparagine, P represents proline, R represents arginine, S represents serine, T represents threonine, V represents valine, W represents tryptophan, and Y represents tyrosine, each peptide being represented by the sequence of amino acids that are continuous from the N-terminus and spaced at every fifth amino acid). Preferably, the type IV collagen-like immunoreactive peptide is homologous to three or more amino acid sequences in the amino acid sequences described above. Note that the amino acid sequences 1) to 5) are designated by specific numbers (No. yp13, etc).

Furthermore, the isolated, chronic nephritis-derived biological sample has an anti-type IV collagen antibody and immunologically reacts with type IV collagen including at least one member selected from the group consisting of at least one chain selected from alpha 1 to alpha 6 chains as a constituent alpha chain, at least one region selected from 7S, the central helical domain, and NC1 as a constituent region, and a peptide having 3 to 35 amino acids as a constituent peptide. Furthermore, the isolated, chronic nephritis-derived biological sample is not limited to a biological sample derived from human nephritis, but may be a biological sample derived from animal nephritis as long as it is a biological sample derived from nephritis. Examples of the chronic nephritis-derived biological sample include urine, serum, kidneys, kidney extracts, and kidney cultures. Preferably, urine is used. In the case of an animal-derived biological sample, it is preferable to use the biological sample while comparing it with an "isolated, nephritis-derived biological sample" of human chronic nephritis.

Preferably, such urine is frozen during storage and defrosted for use, defrosted urine is homogeneously dispersed in phosphate buffered saline (hereinafter referred to as "PBS"), precipitates are removed after centrifugation, the resulting supernatant fluid is dried with a freeze-dryer, and the freeze-dried product is dissolved in PBS (pH 7.4). Furthermore, physiological saline or distilled water for injection may be used instead of PBS. In order to maintain high titer, other processes, such as sterilization and bacteria elimination, are carried out. That is, by using precautions necessary for pharmaceutical makers dealing with biologically derived pharmaceutical products, injections or internal agents can be produced. Furthermore, antibodies purified with an affinity column on which antigen NC1 is immobilized or obtained by ammonium sulfate precipitation may be diluted again so as to adjust their concentrations. Alternatively, immunoglobulin as an antibody may be purified from serum or kidneys.

Furthermore, an antibody of a type IV collagen-like immunoreactive peptide of the present invention is characterized in that it immunologically reacts with the type IV collagen-like immunoreactive peptide, and immunologically reacts with the type IV collagen-like immunoreactive peptide in the same manner as an isolated, chronic nephritis-derived biological sample.

Furthermore, a method for selecting a type IV collagen-like immunoreactive peptide of the present invention is characterized in that, by using an isolated, chronic nephritis-derived biological sample as a ligand, the type IV collagen-like immunoreactive peptide which immunologically reacts with the chronic nephritis-derived biological sample is selected. By using the isolated, chronic nephritis-derived biological sample as a ligand, it is possible to select the type IV collagen-like immunoreactive peptide useful for detecting nephritis.

In the method for selecting a type IV collagen-like immunoreactive peptide of the present invention, the isolated, chronic nephritis-derived biological sample and type IV collagen to be used may be the same as those described above. Furthermore, the type IV collagen-like immunoreactive peptide to be selected may be the same as that described above.

A method for screening an immunoreactive antibody of the present invention is characterized in that it uses the type IV collagen-like immunoreactive peptide. The number of amino acids of the type IV collagen-like immunoreactive peptide is preferably 3 to 35, and more preferably 10 to 20. Specifically, an immunoreactive antibody can be screened by replacing the chronic nephritis-derived biological sample with an anti-alpha 5 chain NC1 antibody or a peptide antibody derived from anti-alpha 5 chain NC1. Thereby, it is possible to screen an immunoreactive antibody useful for detecting nephritis.

Furthermore, a method for screening an immunoreactive peptide of the present invention is characterized in that it uses the antibody of the type IV collagen-like immunoreactive peptide. The number of amino acids of the type IV collagen-like immunoreactive peptide is preferably 3 to 35, and more preferably 10 to 20. Specifically, an immunoreactive peptide can be screened by replacing a synthetic peptide derived from the alpha 5 chain NC1 with a candidate immunoreactive peptide. Thereby, it is possible to screen an immunoreactive peptide useful for detecting nephritis.

Furthermore, a nephritis model of the present invention is characterized in that it uses, as an inducer, at least one of the type IV collagen-like immunoreactive peptide and the antibody of the type IV collagen-like immunoreactive peptide. Conventionally, glomerular basement membranes (GBMs) and glomerulus-derived NC1 have been used as nephritis-inducing antigens. However, they are acute nephritis models and are not suitable as human chronic nephritis models. Furthermore, a case of a peptide derived from the alpha 3 chain is also known, which is also an acute nephritis model. In the nephritis model of the present invention, by using the type IV collagen-like immunoreactive peptide, it is possible to obtain a specific antigen inexpensively, which is suitable for producing an experimental model for chronic nephritis.

Furthermore, in conventional methods for inducing nephritis in which an antibody (antiserum) against an antigen is used, for example, antibodies against GBM, NC1, and the alpha 3 chain are known, all of which are acute nephritis models. Furthermore, there are no cases in which antibodies against the alpha 5 chain, in particular, antibodies against peptides of the human alpha 5 chain are used. In contrast, the antibody of the type IV collagen-like immunoreactive peptide of the present invention is useful and suitable as a human chronic nephritis model.

As such a nephritis-inducing antigen, NC1 of the alpha 5 chain is particularly preferable. Nephritis models induced by glomerulus-derived NC1 belong to a kind of acute nephritis, and thus most of the anti-NC1 antibodies are close to autoantibodies of Goodpasture syndrome which is acute nephritis. Therefore, it is preferable to use such nephritis models while comparing them with an "isolated, nephritis-derived biological sample" of human chronic nephritis. Although a biological sample derived from a diabetes animal model or a hypertension animal model can be used, it is preferable to use such a biological sample while comparing it with an "isolated, nephritis-derived biological sample" of human chronic nephritis as in the case described above.

Furthermore, a method for detecting chronic nephritis of the present invention is characterized in that it uses at least one of the type IV collagen-like immunoreactive peptide and the antibody of the type IV collagen-like immunoreactive peptide. A kit using the ELISA method is preferable, and thereby early diagnosis of nephritis becomes possible.

Furthermore, a vaccine of the present invention is characterized in that it uses at least one member selected from the group consisting of the type IV collagen-like immunoreactive peptide and the antibody of the type IV collagen-like immunoreactive peptide, and the vaccine can be used as a preventive agent or a therapeutic agent for nephritis. Furthermore, a therapeutic agent for nephritis is characterized in that it contains the vaccine. The vaccine or the therapeutic agent for nephritis of the present invention is not particularly limited as long as it contains the type IV collagen-like immunoreactive peptide or the antibody of the type IV collagen-like immunoreactive peptide. For example, yp12 (SEQ ID NO: 6) or the like is dissolved in water, and administration of the resulting agent in the form of solution can inhibit nephritis, etc.

Furthermore, the present invention relates to an apparatus for purifying nephritic blood (including serum and plasma), which can be used as a medical appliance. The principle is in that a target antibody or a target antigen in nephritic blood is brought into contact with a ligand (corresponding antigen or antibody) immobilized on a carrier and having an adsorption function so as to be removed by adsorption. When the target antibody in nephritic blood is an anti-type IV collagen antibody, an antibody of anti-constituent region thereof, or an antibody of anti-constituent peptide thereof (regardless of the length of the constituent peptide), a type IV collagen-like immunoreactive peptide which reacts with an isolated, chronic nephritis-derived biological sample is used as the corresponding ligand antigen.

When the target antigen in nephritic blood is type IV collagen, a constituent region thereof, or a constituent peptide thereof (regardless of the length of the constituent peptide), the corresponding ligand antibody is an anti-type IV collagen-like immunoreactive peptide antibody.

As the ligand, an antibody corresponding to the target antigen or an antigen corresponding to the target antibody is preferable. Instead of the antigen corresponding to the target antibody, protein A or protein G may be used. However, in such a case, there is a possibility that immunoglobulin other than the target antibody may be removed from the blood.

In the process of purifying nephritic blood, preferably, blood is taken from the brachial vein of a patient with nephritis and separated by a plasma separation membrane (or separator) into a plasma component and a blood cell component. Of course, it may be possible to use whole blood instead of separating into the plasma component and the blood cell component. However, in such a case, normal components, such as albumin, other than the target substance come into contact with unnecessary objects outside the body. The separated plasma component is passed through a column having a carrier inside on which a ligand (antigen or antibody corresponding to the target substance) having an adsorption function is immobilized so that the target substance is removed by adsorption, and then the plasma component is mixed with the blood cell component and returned into the body. By performing such a series of steps for purifying blood aseptically and mechanically, the purification can be applied to a medical device. Furthermore, instead of using one column, an antibody column corresponding to the target antigen and an antigen column corresponding to the target antibody may be used.

The antibody column is preferably an anti-alpha 5 chain antibody column, more preferably an anti-alpha 5 chain NC1 antibody column, and still more preferably an antibody column corresponding to the alpha 5 chain-derived peptide which immunologically reacts with an isolated, chronic nephritis-derived biological sample.

The antigen column is preferably an alpha 5 chain column, more preferably an alpha 5 chain NC1 column, and still more preferably a column of the alpha 5 chain-derived peptide which immunologically reacts with an isolated, chronic nephritis-derived biological sample.

The present invention will be described in detail below with reference to the examples.

EXAMPLES

1. Anti-NC1 Antibody Measurement Method

An anti-NC1 antibody measurement method was developed using ELISA in which NC1 (bovine glomerulus-derived, yield 0.0025%) was used as an antigen, and serum and urine were measured. FIG. 1 is a graph showing the comparison (anti-NC1 antibody) between healthy subjects and persons with high urinary albumin level. In FIG. 1, the broken line indicates the cutoff value (0.072), which corresponds to average OD (0.028)+2SD (0.044) of 7 cases with normal urinary albumin level and normal blood sugar level. In FIG. 1, the 12 cases in the left side (Alb (mg/mL)<30) include, in addition to cases with normal urinary albumin level and normal blood sugar level (7 cases), cases with normal urinary albumin level and high blood sugar level (5 cases). The results were that the anti-NC1 antibody was detected in high frequency not only from the serum of patients with Goodpasture syndrome, but also from the serum and urine of persons with high urinary albumin level (FIG. 1) and the serum of dialysis patients.

Specimens of urine of patients diagnosed with nephritis were measured. Eighty percent or more of the nephritis specimens was positive, with the average measurement value of healthy subjects+2SD being the cutoff value. The result suggested the possibility that NC1 was not only the antigen for Goodpasture syndrome, but also was a common antigen for nephritis.

Figure 2:
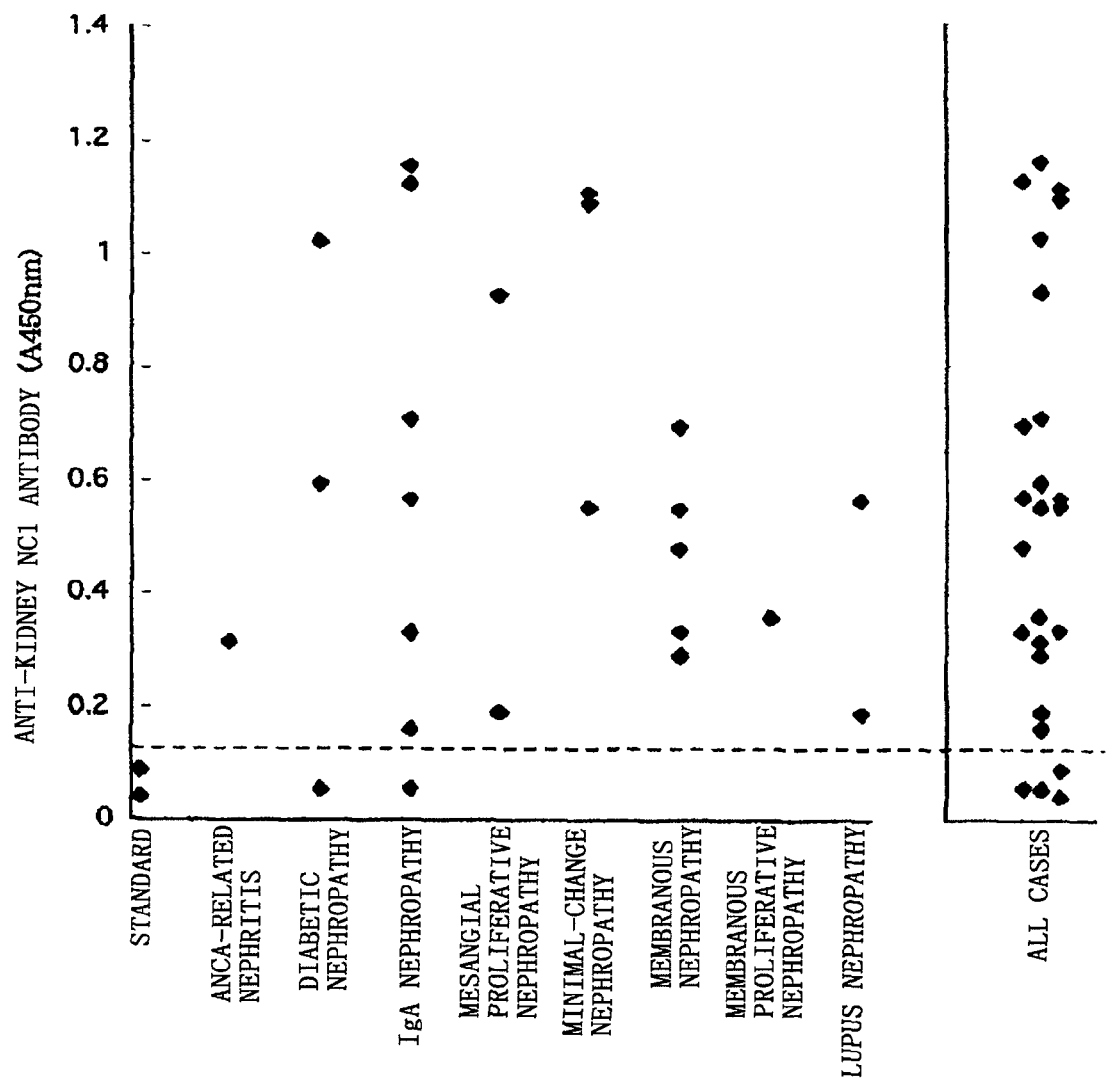
FIG. 2 is a graph listing diseases and their levels of anti-NC1 antibody.

Next, detection of the anti-NC1 antibody for each disease was measured by the same method as that described above. FIG. 2 is a graph listing diseases and their levels of anti-NC1 antibody. Usually, chronic nephritis develops gradually over years or 10 or more years. The anti-NC1 antibody was also detected in diabetic nephropathy or the like, which is secondary nephropathy that usually develops gradually as in chronic nephritis, and there was no particular relationship between the diagnosed disease name and the anti-NC1 antibody level (FIG. 2). Consequently, it was believed that there was a common antigenic site in nephritis.

Figure 3:
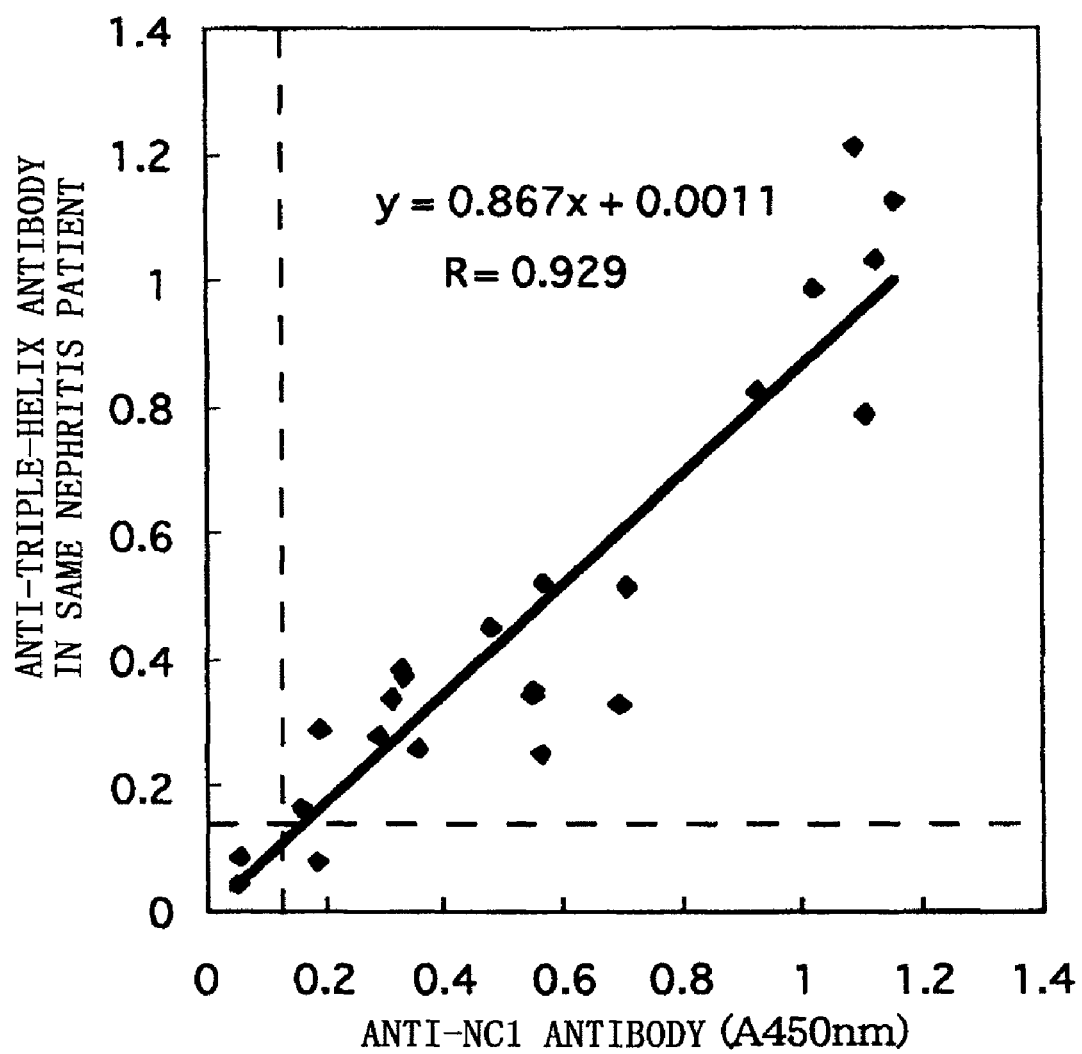
FIG. 3 is a graph showing the correlation between the anti-triple-helix antibody and anti-NC1 antibody in the same nephritis patient.

Furthermore, a triple helix region (including 7S and the central helical domain (TH), hereinafter referred to as "triple helix") having a triple-helical structure of bovine kidney-derived type IV collagen was purified and used as an antigen in place of NC1, and the anti-triple-helix antibody was measured. FIG. 3 is a graph showing the correlation between the anti-triple-helix antibody and anti-NC1 antibody in the same nephritis patient. The anti-NC1 antibody and the anti-triple-helix antibody had a correlation of 90% or higher. Although NC1 and the triple helix had completely different structures and amino acid sequences, they immunologically reacted in the same manner with respect to nephritis. This indicated that the antigen may be 7S or the central helical domain (TH) constituting the triple helix in the same alpha chain (FIG. 3).

2. Method for Finding Reactive Antigenic Site from Type IV Collagen using Isolated, Chronic Nephritis-derived Biological Sample (Hereinafter Referred to as "Biological Sample") as Detection Antibody As the biological sample acting as a detection antibody, urine was directly used. However, serum and kidneys (including kidney extracts and cultures), which are specimens derived from nephritis, may also be used, and adjusted immunoglobulin may also be used. Furthermore, as the biological sample, not only human nephritis-derived samples, but also animal nephritis-derived samples (Bessatsu-Igaku no Ayumi (Supplementary volume-Journal of Clinical and Experimental Medicine), Renal disease state of arts 2003-2005, Ishiyaku Publishers, Inc.) can be used. As the peptide acting as the reactive antigen, a synthetic peptide having the primary sequence was used. However, a chimera peptide, a recombinant peptide, or a peptide produced by any other method may be used. As the amino acid sequence, NC1 of the alpha 5 chain was used. However, NC1 of other alpha chains may be used as long as it reacts with the biological sample. Furthermore, as the amino acid sequence, the alpha 5 chain is preferable in the case of the triple helix (7S and/or the central helical domain). However, the amino acid sequences of other alpha chains may be used as long as they react with the biological sample. The length of the peptide acting as the antigen is preferably 3 to 35 amino acids in view of cost and efficiency, and most preferably 10 to 20 amino acids in view of also achieving ease of production of the antibody. Furthermore, the search method and results are not limited to the alpha 5 chain, and also apply to the search of all alpha chains of type IV collagen and the results of search.

Selection of a biological sample using type IV collagen NC1 was measured by the ELISA method. A biological sample (urine in this example) diluted fourfold with PBS (pH 7.4) was placed in a 96-well microplate which was coated with 100 μl/well (10 μg/mL) of bovine glomerulus-derived NC1, and incubation was performed for two hours at 23° C. (hereinafter at the same temperature), followed by washing with PBS. An enzyme (HRP) labeled anti-human IgG antibody solution was added thereto, and incubation was performed for one hour, followed by washing. A substrate solution (TMB) was added thereto, and after a predetermined period of time of 5 to 30 minutes (10 minutes in this case), a reaction termination solution (1 N sulfuric acid) was added to the reaction mixture. Immediately thereafter, absorbance (OD) was measured at 450 nm.

FIG. 4 shows the comparison of measured data (anti-NC1 antibody) with respect to chronic nephritis TD38, diabetic nephritis TD42 and healthy subjects (TD31 to 37 and TD39 to 41). In this experiment, the anti-NC1-IgG antibody in urine was measured, enzyme-labeled anti-human IgG antibody (human HRP326) diluted to 4,000-fold was used, and the reaction was carried out for 60 minutes. In FIG. 4, the cutoff value is OD. 0.443 (healthy subjects/n=10; average 0.255+2SD. 0.188), 1.008 for chronic nephritis (hereinafter "A"), and 2.696 for diabetic nephritis (hereinafter "B"). As a result, the urine specimens having a high anti-NC1 antibody level selected could be directly used as "isolated, nephritis-derived biological samples (biological samples). Some of them were divided into small portions, frozen, and stored.

Preparation of Isolated, Nephritis-Derived Biological Sample (Biological Sample)

The antibodies degrade in acidic urine. Therefore, the urine specimen stored in the frozen state was defrosted while being shaken at 18° C. overnight so that the urine specimen was homogeneously dispersed together with precipitates. Then, the defrosted urine was diluted exactly fourfold with PBS, and while shaking at 18° C. for 24 hours, a homogeneously dispersed liquid was prepared. The dispersed liquid was subjected to centrifugation at about 3,000 G for 5 minutes, and the precipitates were removed. The resulting supernatant fluid was measured and dried with a freeze-dryer. Sterile PBS (pH 7.4) in the amount originally measured was added to the freeze-dried product, the container was washed out, and PBS was recovered. By repeating this operation four to five times, a pH neutralized, stable "biological sample" was obtained. Then, the anti-NC1 antibody level was measured again, and the measured OD value was considered as the titer per 1 mL. Physiological saline or distilled water for injection may be used instead of PBS. In order to maintain high titer, other processes, such as sterilization and bacteria elimination, are carried out. That is, by using precautions necessary for pharmaceutical makers dealing with biologically derived pharmaceutical products, injections or internal agents can be produced. Furthermore, the biological sample can also be used as an inducer for a nephritis model. Moreover, as "biological samples", antibodies purified with an affinity column on which antigen NC1 is immobilized or obtained by ammonium sulfate precipitation may be diluted again so as to adjust their concentrations. Alternatively, immunoglobulin as an antibody may be purified from serum or kidneys. In particular, in the case of autologous administration of a biological sample obtained from the nephritis patient himself or herself, because of its high affinity, an abnormal immunoreaction does not easily occur even if the biological sample is used as an injection. Furthermore, an oral administration agent is also preferable in view of oral tolerance.

Furthermore, animal-derived biological samples may also be used. As the inducer, NC1 of the alpha 5 chain is particularly preferable. Nephritis models induced by glomerulus-derived NC1 belong to a kind of acute nephritis, and thus most of the anti-NC1 antibodies are close to autoantibodies of Goodpasture syndrome which is acute nephritis. Therefore, it is preferable to use such nephritis models while comparing them with an "isolated, nephritis-derived biological sample" of human chronic nephritis. Although a biological sample derived from a diabetes animal model or a hypertension animal model can be used, it is preferable to use such a biological sample while comparing it with an "isolated, nephritis-derived biological sample" of human chronic nephritis as in the case described above.

Method for Selecting type IV Collagen NC1-like Immunoreactive Peptide using Isolated, Nephritis-derived Biological Sample (Biological Sample)

Among a plurality of published amino acid sequences, the present inventor has used the proposed sequences described in the document by Ninomiya et al. (pp235-260 In Extra cellular matrix-cellular interaction: Molecules to diseases, ed by Ninomiya Y et al. Japan Sci Press, Tokyo/S Karger, Basel. 1998) (FIG. 5). The number of amino acid residues of NC1 per alpha chain is about 230. Since six alpha chains exist, the total number of amino acid residues to be checked is 1,380 for NC1.

Preliminary Test

A preliminary test was carried out, using the ELISA method, in which NC1 as the antigen for coating was replaced with synthetic peptides. The measurement conditions were: antigen concentration: 10 μg/mL (10 mM PBS), 100 μL/well; blocking agent: Block Ace (manufactured by Dainippon Pharmaceutical Co., Ltd.) diluted to 25%, 250 μL/well; urine: human 20- to 100-fold dilution; second antibody (enzyme-labeled anti-human IgG antibody): ×800; and substrate solution: TMB (+) (manufactured by DAKO Corp). The specimen was diluted to 20- to 100-fold, unlike the original fourfold dilution of NC1 as the antigen. The results were that in both the specimen A (chronic nephritis) and the specimen B (diabetic nephritis), compared with the antigen peptide 301 (20 amino acid residues that are continuous from the N-terminus on alpha 3 chain NC1), the immunoreaction was strong in the antigen 501 (20 amino acid residues that are continuous from the N-terminus on alpha 5 chain NC1). Accordingly, a main test was carried out using NC1 of the alpha 5 chain. Note that 301 contained the amino acid sequence about 5 to 18 from the N-terminus on the alpha 3 chain corresponding to Goodpasture syndrome specified by computer software. Furthermore, it was possible to check alpha chains other than the alpha 5 chain, such as 301. Furthermore, in each of 301 and 501, the antibody level in the urine of nephritis patients was clearly higher than that of the urine of healthy subjects, and was sufficiently distinguishable. Therefore, it was possible to use both antigens as nephritis detection reagents.

Screening of Antigenic Site on Alpha 5 Chain NC1

A test was carried out using the ELISA method, in which NC1 as the antigen for coating was replaced with synthetic peptides, under the same conditions as those described above. FIG. 6 shows the comparison with respect to NC1-like antigenicity among chronic nephritis No. 38, diabetic nephritis No. 42, IgA nephropathy, and healthy subjects Nos. 31, 32, and 33.

The peptides of the alpha 5 chain were prepared as described below. Fifteen synthetic peptides were prepared from the whole region of the alpha 5 chain NC1, in which a first unit of 20 amino acid residues was selected from the N-terminus, and subsequent units, each containing 20 amino acid residues, were selected with 5 amino acid residues overlapping each other (hereinafter referred to as yp01 to yp15 (H4NA5-1 to 5-15 in FIG. 6), yp15 containing more than 20 amino acid residues). The results were that the specimen A (chronic nephritis: No. 38) strongly reacted with yp05 (SEQ ID NO: 9), 08 (SEQ ID NO: 8), 13 (SEQ ID NO: 5), 10 (SEQ ID NO: 7), and 12 (SEQ ID NO: 6); the specimen B (diabetic nephritis: No. 42) strongly reacted with yp10 (SEQ ID NO: 7), 13 (SEQ ID NO: 5), 08 (SEQ ID NO: 8), 05 (SEQ ID NO: 9), and 12 (SEQ ID NO: 6); and IgA nephropathy strongly reacted with yp08 (SEQ ID NO: 8), 05 (SEQ ID NO: 9), 10 (SEQ ID NO: 7), 13 (SEQ ID NO: 5), and 12 (SEQ ID NO: 6), indicating the coincidence of the peptide groups with high reactivity. Thus, the five peptides were antigenic sites common to the specimen A, the specimen B, and IgA nephropathy which were derived from different diseases. As described above, bovine glomerulus-derived NC 1 and triple helix have substantially the same reactivity with nephritis urine specimens, and both are considered to be common antigens to nephritis. Thus, the triple helix (7S and/or the central helical domain) of the alpha 5 chain and peptides thereof can be considered as immunoreactive peptide candidates. The whole alpha 5 chain may be used as an antigen. However, in such a case, a time-consuming process is required.

As described above, the "biological sample" is a ligand effective for screening NC1-like immunoreactive peptides. It was also possible to use the found peptides and antibodies thereof as ligands for detecting corresponding antibody or antigen peptides in the same manner. In particular, antibodies prepared from immunoreactive peptides, regardless of whether they were monoclonal antibodies or polyclonal antibodies, were effective for detecting new immunoreactive peptides instead of the "biological sample". All of the peptides found from the alpha 5 chain showed a large difference in reaction between urine specimens of nephritis and urine specimens of healthy subjects (FIG. 6), and could be used for reagent kits for detecting nephritis. The immunoreactive peptides of the present invention have type IV collagen-like immunoreactivity, and are not limited to peptides derived from the alpha 5 chain.

3. Method for Screening New Alpha 5 Chain NC1-like Immunoreactive Peptide

In the process of screening candidate immunoreactive peptide, the synthetic peptide derived from the alpha 5 chain NC1 was replaced with a candidate immunoreactive peptide. The biological sample may be replaced with an anti-alpha 5 chain NC1 antibody or an anti-alpha 5 chain NC1-derived peptide antibody. In such a case, the labeled antibody was selected so as to correspond to the animal from which the antibody was derived.

The peptide used as the candidate immunoreactive peptide may have any sequence and is not limited to type IV collagen as long as it is a peptide having immunoreactivity equal to or higher than the proposed peptides derived from alpha 5 chain NC1. Furthermore, the proposed peptides may be shortened, lengthened, altered, substituted, or modified, or may be combined to form an amino acid sequence. For example, yp12 (SEQ ID NO: 6) and yp13 (SEQ ID NO: 5) may be combined. In order to partially alter the proposed peptide, simply, an animal-derived sequence may be used. Furthermore, in the peptides using a part of the amino acid sequence of the alpha 5 chain NC1, any amino acid sequence could be used as long as it had imminoreactivity higher than that of NC1 extracted and purified from the living body.

The present invention is applicable to the whole amino acid sequence of the alpha 5 chain including the triple helix (7S and/or the central helical domain). A peptide having a smaller region than the whole region of the alpha 5 chain and having good triple helix-like or NC1-like immunoreactivity is preferable. A shorter peptide having better immunoreactivity is more preferable. In terms of cost and effect, the length of peptide is preferably 3 to 35 amino acids, and such a peptide can be selected by the ELISA method described above, although not limited thereto.

The above can be applied to other alpha chains in the same manner, and thus, instead of the biological sample, various antibodies, such as antibodies to peptides derived from the regions, such as NC1, 7S, and the central helical domain, the individual alpha chains, and type IV collagen may be used. In the case of animal species other than the biological sample, the components of the reagent for human use described above were adjusted so as to meet the animal species. Furthermore, when the present invention is applied to the other alpha chains, preferably, reactivity with an isolated, nephritis-derived biological sample is confirmed in advance.

The immunoreaction is not limited to an enzyme immunoreaction. Examples of the immunoreaction also include an AB method, RIA, an immunoluminescence method, a precipitation reaction, and an agglutination reaction. As an enzyme-labeled antibody, either a polyclonal or monoclonal antibody may be used. The antibody may be radiolabeled, luminescence-labeled, or non-labeled. The reaction mode is not limited to a sandwich method, but a competitive method or the like may be used. Glass, a magnetic substance, or a latex may be used instead of a plate. Alternatively, without using any of these, the solid phase method may not be employed.

When a plate is coated with a peptide, the substance for coating may be applied through avidin, biotin, or a combination thereof. As the peptide with which the plate is coated, a plurality of peptides may be mixed. Alternatively, a selected mixed peptide specimen may be divided into constituent peptides, and selection may be made therefrom. The peptide preparation is not limited to synthesis, and it is possible for persons skilled in the art to employ any method used in the other fields. Furthermore, the second antibody is not limited to the anti-specimen IgG antibody. Although an anti-specimen IgM antibody, an anti-specimen IgA antibody, or an anti-specimen immunoglobulin antibody may be used, the anti-specimen IgG antibody is preferable.

4. Preparation of Nephritis Model using Immunoreactive Peptide as Inducer

The selected peptides can be used as an inducer of nephritis independently and/or in combination with each other. Although yp08 (SEQ ID NO: 8) and yp12 (SEQ ID NO: 6) were used as peptides and rabbits and guinea pigs were used as animals, the peptides, animals, and administration methods are not limited thereto.

Peptides 0.3 mg/mL (0.15 mg only for initial administration) together with the same amount of FCA were intradermally administered to rabbits (female) once in two weeks, four times in total. The results were that yp08 (SEQ ID NO: 8) showed urinary protein (#2; +2) and yp12 (SEQ ID NO: 6) showed urinary protein (#1; +2), all of which were positive.

Furthermore, in the ELISA method in which themicroplate was coated with the peptide yp12 (SEQ ID NO: 6) (10 µg/mL), in 7 weeks after the initial administration, at a dilution of 32,000 fold, the antibody level in serum reached 3.00, which is in the vicinity of the upper limit of measurement of the absorptiometer.

ELISA antibody level; yp08 (SEQ ID NO: 8) (#2×8,000; A450 nm/3.00)

yp12 (SEQ ID NO: 6) (#1×32,000; A450 nm/3.00)

Peptides 0.1 mg/mL together with the same amount of FCA were intradermally administered to guinea pigs (female) once in two weeks, four times in total. The results were that yp12 (SEQ ID NO: 6) showed urinary protein (#1; +1, #2; ±, #3; ±), all of which were slightly positive. This means that human nephritis gradually progresses, indicating that they are suitable models.

Furthermore, in the ELISA method in which the microplate was coated with the peptide yp12 (SEQ ID NO: 6) (10 µg/mL), in 7 weeks after the initial administration, at a dilution of 8,000 fold, the antibody level in guinea pig serum reached 3.00, which is in the vicinity of the upper limit of measurement of the absorptiometer. Furthermore, intra-abdominal administration to rats or mice of these anti-immunoreactive peptide antibodies (antiserum) enabled production of models of nephritis which was weak, close to that of human, and slowly progressive, unlike the administration of conventional anti-NC1 antibodies (antiserum).

5. Inhibition of Nephritis by Immunoreactive Peptide

During an acclimation period of one week after purchase of two guinea pigs, yp12 (SEQ ID NO: 6) dissolved in water was administered in a total amount of 5 to 10 mg to the guinea pigs. Then, nephritis was induced as described above. No urinary protein was observed (#1; −, #2; −), and nephritis urine was not detected.

Oral administration of immunoreactive peptides corresponds to vaccines and therapeutic agents for nephritis. The immunoreactive peptides and antibodies thereof could be used for oral administration agents, desensitization therapies, and injections. Although a similar example is described in Japanese Unexamined Patent Application Publication No. 2000-214163, in the present invention, by further specifying peptides, the effect is enhanced.

6. Elisa Kit Using Antibody Against Immunoreactive Peptide

ELISA methods are commonly used measurement methods for detecting an antigen or an antibody, and there is not much difference in measuring procedure. Therefore, examples in which the antibodies described above are combined are shown herein.

In measurement of "antigen NC1" by the sandwich ELISA method, instead of "the anti-NC1 monoclonal antibody and the anti-NC1 antibody (guinea pig)", using any of the combinations of "the anti-yp12 antibody (rabbit) and the anti-yp12 antibody (guinea pig)" and "the anti-NC1 monoclonal antibody and the anti-yp12 antibody or the anti-yp08 antibody", it was possible to measure NC1. Nephritis in the early stage was detected using urine as a specimen. With respect to the measurement range, for example, in the case of "an anti-NC1 monoclonal antibody (PCT/JP2005/002669) and an anti-NC1 antibody (guinea pig)", in which a microplate was coated with the anti-NC1 monoclonal antibody (2 µg/mL), and the AB method (Avidion-HRP×4,000) was performed using the anti-NC1 antibody (guinea pig) (IgG AP-Biotin 0.95 mg/mL), NC1 could be measured in a very small amount in the range of 50 ng/mL to 1 ng/mL and detected from urine of the case of nephritis, in particular, diabetic nephritis in the early stage. Since it is not possible to detect the antigen from urine in advanced cases of nephritis, a diagnostic agent for diseases in the early stage can be produced. In such a case, using the sample from nephritis as a specimen, antibodies (including anti-NC1 antibodies) corresponding to yp08 (SEQ ID NO: 8) and yp12 (SEQ ID NO: 6) on an antigen solid-phase plate were detected. Furthermore, the combinations of "the anti-yp12 antibody (rabbit) and the anti-yp12 antibody (guinea pig)" and "the anti-NC1 monoclonal antibody and the anti-yp12 antibody or the anti-yp08 antibody" can measure yp12 (SEQ ID NO: 6) or yp08 (SEQ ID NO: 8), and thus can be used as laboratory reagents.

Even in the case where a triple helix (7S and/or the central helical domain) derived immunoreactive peptide is selected by the same method as that used for the alpha 5 chain NC1, and an antibody against the selected immunoreactive peptide is used, it is also possible to measure the triple helix (7S and/or the central helical domain) and/or the immunoreactive peptide.

By using isolated, nephritis-derived biological samples, it was possible to select type IV collagen-like immunoreactive peptides. Furthermore, the selected type IV collagen-like immunoreactive peptides could substitute for type IV collagen, and were useful for diagnostic agents for nephritis, therapeutic agents for nephritis, therapeutic devices for nephritis, elimination of antibodies from biological samples, and collection of antibodies. Furthermore, the anti-type IV collagen-like immunoreactive peptide antibodies were useful for diagnostic agents for nephritis, therapeutic agents, therapeutic devices for nephritis, elimination of antigens from biological samples, and collection of antigens.

The invention claimed is:

1. A type IV collagen-like immunoreactive peptide, consisting of an amino acid sequence selected from the group consisting of SEQ ID NO: 5, SEQ ID NO: 6, SEQ ID NO: 7, SEQ ID NO: 8, and SEQ ID: NO 9, wherein the peptide immunologically reacts with an isolated, chronic nephritis-derived biological sample.

2. The type IV collagen-like immunoreactive peptide according to claim 1, wherein the isolated, chronic nephritis-derived biological sample is urine.

3. The type IV collagen-like immunoreactive peptide according to claim 2, wherein the urine is frozen during storage and defrosted for use, defrosted urine is homogeneously dispersed in phosphate buffered physiological saline, precipitates are removed after centrifugation, the resulting supernatant fluid is dried with a freeze-dryer, and the freeze-dried product is dissolved in phosphate buffered physiological saline.

* * * * *